United States Patent

Huskey

Patent Number: 5,843,260
Date of Patent: Dec. 1, 1998

[54] METHOD OF MANUFACTURING A SOFT DIAPER TAPE

[75] Inventor: Richard A. Huskey, Mentor, Ohio

[73] Assignee: Avery Dennison Corporation, Painesville, Ohio

[21] Appl. No.: 909,083

[22] Filed: Aug. 14, 1997

Related U.S. Application Data

[62] Division of Ser. No. 676,002, Jul. 5, 1996, Pat. No. 5,738, 930, which is a division of Ser. No. 271,262, Jul. 6, 1994, Pat. No. 5,599,620, which is a continuation of Ser. No. 57,043, May 3, 1993, abandoned.

[51] Int. Cl.⁶ .................................................. A61F 13/16
[52] U.S. Cl. .................. 156/153; 156/209; 156/244.24; 264/129; 264/210.2; 604/389
[58] Field of Search ..................................... 156/153, 209, 156/244.24, 244.18; 264/129, 210.2; 604/389

[56] References Cited

U.S. PATENT DOCUMENTS

| | | |
|---|---|---|
| 3,932,328 | 1/1976 | Korpman . |
| 4,237,889 | 12/1980 | Gobran . |
| 4,376,147 | 3/1983 | Byrne et al. ............................. 428/167 |
| 4,436,520 | 3/1984 | Lipko et al. ......................... 604/389 X |
| 4,546,029 | 10/1985 | Cancio et al. ........................... 428/141 |
| 4,861,635 | 8/1989 | Carpenter et al. . |
| 5,026,446 | 6/1991 | Johnston et al. . |
| 5,147,347 | 9/1992 | Huang et al. . |
| 5,158,557 | 10/1992 | Noreen et al. . |
| 5,328,653 | 7/1994 | Hyde et al. . |

FOREIGN PATENT DOCUMENTS 0 394 550  10/1990  European Pat. Off. .

*Primary Examiner*—Jeff H. Aftergut
*Attorney, Agent, or Firm*—Pearne, Gordon, McCoy & Granger LLP

[57] ABSTRACT

A fastener tab for disposable diapers has improved tactile softness provided by surface morphologies of preselected projection and/or relief dimensions.

5 Claims, 2 Drawing Sheets

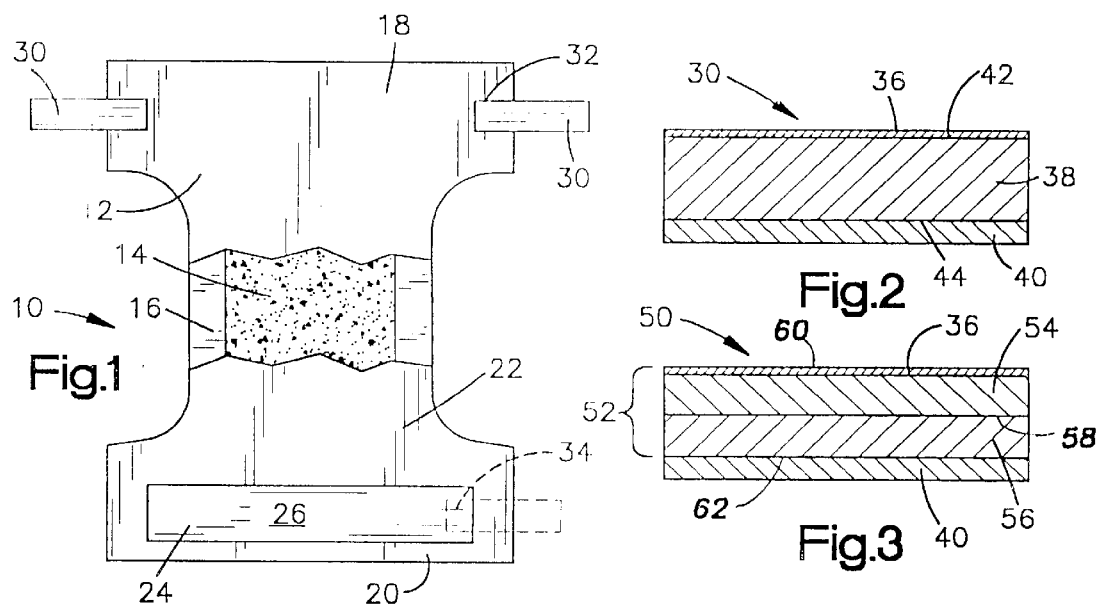
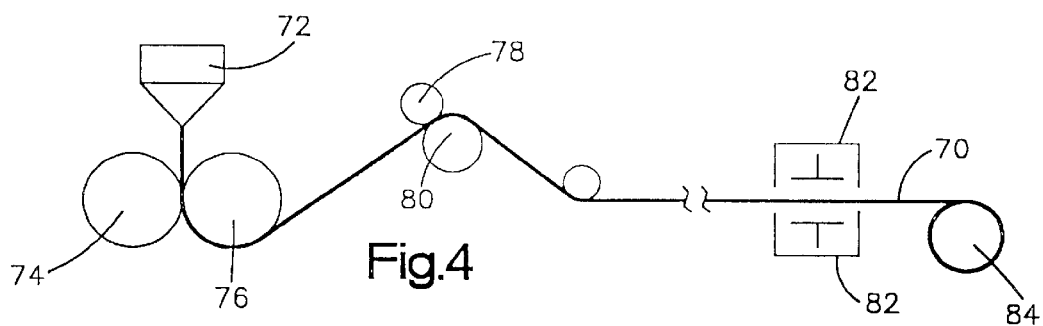
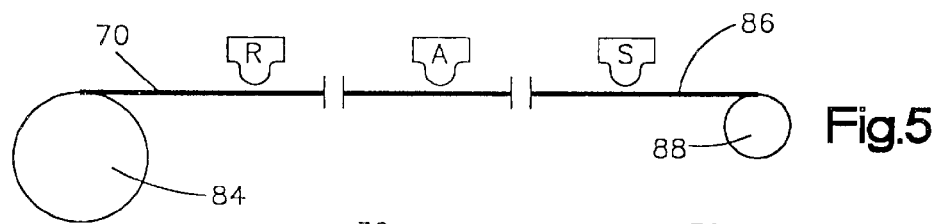
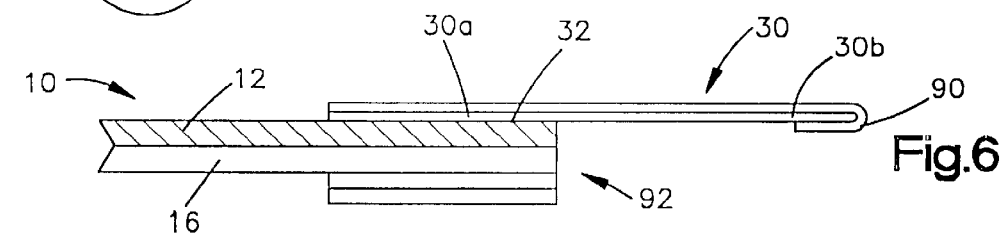
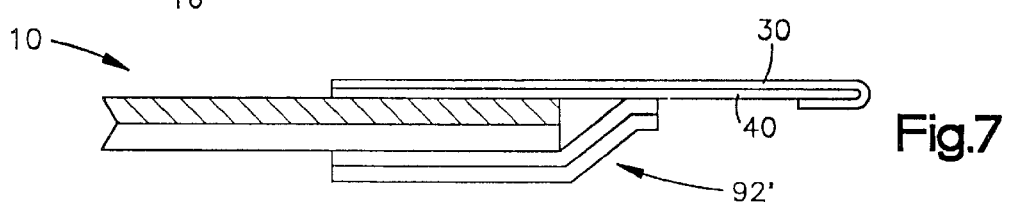

METHOD OF MANUFACTURING A SOFT DIAPER TAPE

This is a division of application Ser. No. 08/676,002, filed Jul. 5, 1996, now U.S. Pat. No. 5,738,930, which is a division of application Ser. No. 08/271,262, filed Jul. 6, 1994, now U.S. Pat. No. 5,599,620, which is a continuation of application Ser. No. 08/057,043, filed May 3, 1993, now abandoned.

BACKGROUND OF THE INVENTION

This invention relates to tabs for disposable diapers, geriatric briefs, surgical drapes or other articles requiring a fastener tab and to tapes convertible to make such tabs.

In the manufacture of disposable diapers, it is typical practice for the diaper manufacturer to provide diaper fastener tabs fixed to the diaper proper. Each tab is permanently attached at one end thereof to the diaper shell at a "factory joint" at the rear of the diaper. The other end of the tab is arranged for fastening and refastening the diaper closed to a reinforcing tape or landing zone at a "user joint" at the front of the diaper. To that end, the tab includes a polymeric substrate or backing film and an adhesive layer.

It is desirable to provide such tabs with an increased softness. Such softness may be provided for aesthetic and/or functional purposes as discussed more fully below.

Tactile softness may be desirable solely for aesthetic purposes as well as for infant comfort. Pliant softness characterized by highly flexible or conformable film deformation properties provides infant comfort by reducing the tendency to chafe or irritate the infant's skin upon contact. To some extent, both tactile and pliant film softness may combine to reduce chafing and irritation.

Heretofore, tactile and/or pliant film softness have been provided by formulation of the polymeric film with polymers of relatively lower modulus. For example, polyethylene homopolymers may be used to provide a relatively soft feeling and highly flexible tab substrate or backing film. Similarly, polyethylene may be combined as a copolymer or physically blended with other polymers such as polypropylene to increase the softness of the resulting copolymer or polymer blend. Other polymers, such as ethylene-vinyl acetate (EVA) may also be used as copolymer or blended constituents.

The use of polyethylene homopolymers, copolymers or blends to achieve tab softness is not been entirely satisfactory since polyethylene tends to cause adhesive aging problems characterized by accelerated rates of decrease of adhesion strength with age. The aging problems are believed to be associated with the tendency of one or more adhesive components to migrate into the polyethylene moiety (polyethylene copolymer or blended material) with swelling of the latter. In the case of polypropylene blends and copolymers with polyethylene, it is believed that no more than about five percent polyethylene by weight may be present in order to avoid unacceptable adhesive aging characteristics.

As compared with films of polypropylene homopolymer, polyethylene copolymers and physical blends tend to be characterized by lower modulus values. Therefore, it is expected that tab substrate or backing films of such polyethylene materials will require slightly higher thicknesses than the 4.2 to 6 mil thicknesses used for polypropylene in order to assure film stability and ease of handling during machine processing. Of course, such polyethylene, polypropylene and/or copolymers thereof at higher thicknesses also tend to result in a cost disadvantage due to the additional material costs and the higher costs of copolymer films as compared with homopolymer films.

The outer side of polymeric fastener tabs have been embossed to provide them with a roughened outer surface. Various embossing patterns have resulted in corresponding degrees of roughness. One convenient measure of surface roughness is provided by the "Ra" roughness average or value measured in angstroms with a Dektak 3030 profile measuring system using a 2.5 um radius stylus. (The Dektak 3030 profile measuring system is manufactured by the Sloan Technology subsidiary of Veeco Instruments Inc. of Santa Barbara, Calif.) The Ra roughness average or value of a surface is defined as the distance between the average peak or projection height and an imaginary median line on the sample surface positioned so that the areas enclosed by the peak portions above the line will be equal to the areas enclosed by the valleys between the peak portions below the line. Hereinafter, such Ra roughness averages or values are reported to indicate the relative roughnesses of surface morphologies.

Prior art diaper fastener tabs have been found to range in roughness from Ra values of 25,000 angstroms to 170,000 angstroms due to various finish processing techniques including embossing. Presumably such roughness is used to avoid the gloss finish otherwise obtained by finish rolling plastic film with a polished steel roll.

It is known from U.S. Pat. No. 5,147,347 to emboss or otherwise texture the outer surface of a diaper shell to provide a non-glossy, matte finish material which the patentee indicates is soft to the touch, provides a more garment-like appearance, and produces less rattling noise when manipulated. It is believed that such diaper shell roughening tends to cause poor adhesive contact efficiency which is associated with the inadvertent "pop-off" release of diaper tabs and/or tears of the diaper shell at the factory joint. The contact efficiency is reduced by surface morphologies of relatively rough characteristics having significant variations in surface projections and/or relief dimensions. In some instances, the contact efficiency is further decreased by roughening of the fastener tab adhesive layer during processing. More particularly, fastener tabs are typically formed of self-wound tapes and the adhesive layer of the wound tape replicates the roughness or embossing pattern of the substrate. The exposed surface of the adhesive layer of the tab is thereby roughened and itself may further inhibit adhesive contact efficiency.

SUMMARY OF THE INVENTION

It has now been discovered that film surfaces of increased tactile softness may be provided by selected film surface morphologies. Such film surface morphologies are characterized by patterns of preselected projection and/or relief dimensions.

The surface morphology may be selected to sufficiently increase the tactile softness of the film to impart acceptable hand sensed softness to a film which would otherwise be perceived as too stiff upon hand manipulation. Thus, the tactile softness achieved by the surface morphology in accordance with the invention enables a degree of masking or concealing of modulus and/or thickness derived film stiffness. In this manner, the surface morphology enables the use of relatively higher modulus and thickness polymeric film materials. However, higher modulus materials are preferably used at relatively lower thicknesses in order to reduce costs and further increase film softness as compared with prior art fastener tab polymeric film substrates or backing films. Herein, backing films having a thickness between 1 to 4 mils are provided. Applicant is not aware of a prior art diaper tab backing film having a thickness of about 4 mils or less.

Another important advantage of the present invention is the ability to avoid the use of polyethylene or other troublesome constituents in the polymeric film material in order to achieve softness. This enables the prior art adhesive aging problems associated with the use of polyethylene to be avoided. Accordingly, the surface morphology enables changes in film compositions, as well as film modulus and thickness properties as discussed above, which cooperate in a synergistic manner to provide films of improved softness, strength and durability.

It is not necessary that film compositions in accordance with the invention be free of all polyethylene. In certain machine processing applications, the film composition may include a small amount of polyethylene (e.g. 0.5 to 3%) to avoid film shattering. Thus, the presence of polyethylene does not inhibit the practice of the invention and, in fact, the softness improvements of the invention may be applied to polyethylene materials.

It has also been found that the film surface morphology may reduce the occurrence of tab "pop-off" disengagement and/or diaper shell tearing. More particularly, the surface morphology may be selected to be sufficiently less rough than that of the prior art tabs or tapes so as to achieve improved adhesive contact efficiency.

The improvements of the invention are obtained with film surface morphologies having Ra values in the range of from about 7,000 angstroms or lower up to about 14,700 angstroms. More preferably, the Ra values will be in the range of from about 8,000 to 10,000 angstroms.

The exact lower limit of the Ra value corresponding with the tactile softness improvements of the invention has not been determined. As a practical matter, lesser improvements in tactile softness may be expected with increasing smoothness approaching that of a gloss finish obtained by forming the film surface with a polished steel roll as such softness improvements become no longer subjectively perceivable by hand manipulation of the film. The gloss finish surface of a film is not deemed to provide desirable tactile properties.

A preferred method of providing film surface roughness is embossing. This may be done immediately following film formation or it may comprise a subsequent processing step.

BRIEF DESCRIPTION OF THE DRAWINGS

In the drawings, all of which are highly diagrammatic and do not show various elements to scale, FIG. 1 is a plan view of a disposable diaper having fastener tabs in accordance with the invention;

FIG. 2 is a cross-sectional view on an enlarged scale of one of the fastener tabs of FIG. 1 prior to its application to the diaper;

FIG. 3 is a cross-sectional view similar to FIG. 2 showing another embodiment of a fastener tab in accordance with the invention;

FIG. 4 is a schematic view showing process steps for making a substrate or backing film for use in making the fastener tab of FIG. 1;

FIG. 5 is a schematic view showing process steps for making and converting a tape to form the fastener tab of FIG. 1;

FIG. 6 is a cross-sectional view on an enlarged scale showing the attachment of one of the fastener tabs at a factory joint to the diaper of FIG. 1;

FIG. 7 is a cross-sectional view similar to FIG. 6 showing the attachment of the fastener tab at a factory joint using a "Y-bond";

DETAILED DESCRIPTION OF THE DRAWINGS

Figure 8:
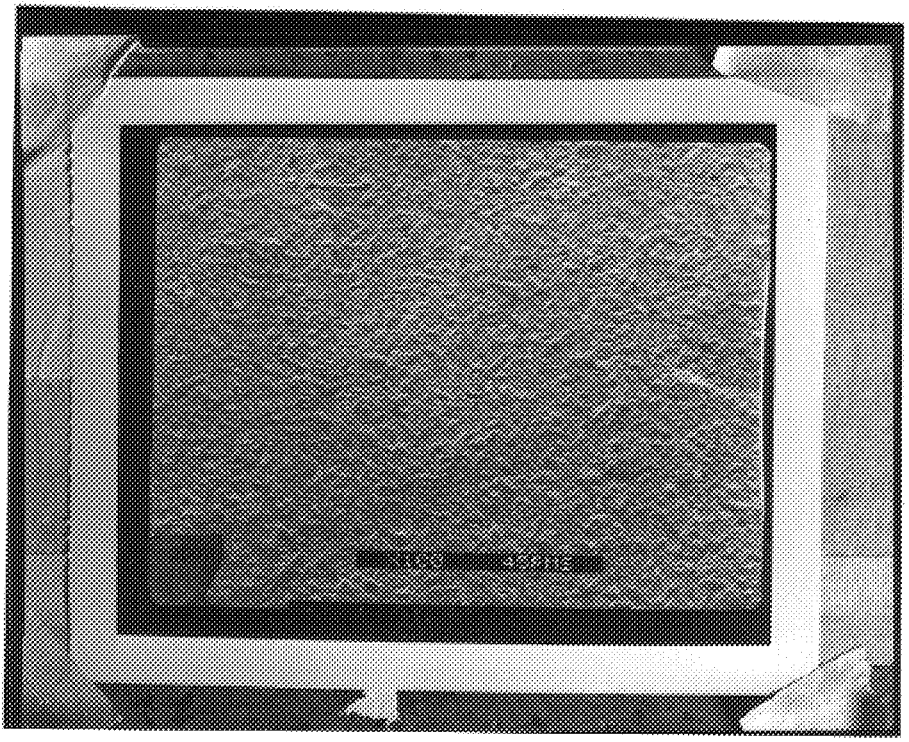
FIG. 8 is a photomicrograph at 100× magnification of the surface of the outer side or embossed side of a polymeric substrate film for a fastener tab in accordance with the invention.

Referring to FIG. 1, a disposable diaper 10 includes a plastic film outer layer or shell 12 and an absorbent layer or body 14 disposed between the shell 12 and a top sheet 16. The top sheet 16 tends to separate an infant from moisture absorbed in the body 14. As shown, the shell 12 and top sheet 16 are coterminous and extend past both the lateral and longitudinal edges of the body 14.

The shell 12 has a front waistband section 18 and a rear waistband section 20 connected by a narrowed intermediate crotch section 22. A reinforcing tape 24 is permanently attached along the front waistband section 18 of the diaper shell 12. The tape 24 provides a landing surface or zone 26 for adhesive connection with a pair of identical fastener or fastening tabs 30 mounted to associated lateral ends of the rear waistband section 20. Each of the tabs 30 has an elongate shape and is sized to extend from a factory joint 32 securing the tab to the diaper shell 12 at the rear waistband section 20 to a user joint 34 (shown in dotted outline) at the landing surface 24 for fastening and refastening the diaper closed about an infant.

Referring to FIG. 2, the tab 30 includes a release layer or coating 36, a polymeric substrate or backing film 38 and an adhesive layer 40. As described more fully below, the release layer 36, film 38 and adhesive layer 40 are of known compositions. However, certain prior art restraints in the selection of the polymeric components of the adhesive layer 40 are removed in accordance with the invention.

The film 38 may be prepared by extrusion or casting techniques with charge formulation or subsequent processing to provide the desired surface morphology as described below. The film 38 includes an outer or exposed side 42 and an inner or adhesive side 44. The exposed side 42 is provided with a selected surface morphology to achieve improved tactile softness. The adhesive side 44 generally has a smoother surface than the exposed side 42.

The surface morphology of the exposed side 42 is characterized by a random roughness or texture within a selected range of roughness. The surface morphology may be provided by any suitable texturing technique including embossing or abrading the film as well as the addition of matting agents to the resin composition of the film. A presently preferred technique comprises embossing the film immediately upon manufacture with an engraved embossing roll having a random pattern. Useful steel embossing rolls having a random roughness pattern provided by a sand blasting technique and a chrome finish coat are disclosed in U.S. Pat. No. 4,436,520. A suitable roll roughness is characterized as having a projection and/or relief profile wherein the root mean square of the projection heights is 45 microinches and the roll is referred to as a "45 RMS roll. A 45 RMS roll results in a film having a Ra value ranging from 9,000 to 13,000 angstroms when used to immediately emboss and chill the extruded film. Increasing RMS roll numbers result in increasing roughness, e.g. 99 RMS corresponds with a Ra value of about 25,000 angstroms and 250 RMS corresponds with a Ra value of from 68,830 to 75,830 angstroms.

The film 38 may be formed of a suitable film forming resin such as a polyolefin homopolymer, copolymer or blend, and it may include other polymeric constituents or additives. Preferred materials include polypropylene homopolymer and copolymers and blends with lesser amounts of other constituents. The polypropylene polymers are preferred since they provide relatively higher moduli in the range of 80,000 to 250,000 psi as measured using ASTM D882-88.

As indicated, the tactile softness improvements of the surface morphologies tend to mask or conceal the hand perceptible stiffness of higher modulus polymers so as to enable the use of thinner films of higher modulus materials. Accordingly, films having modulus values in the range of 80,000 to 250,000 psi and gages less than about 4 mils have been used as backing film for fastener tabs. The advantages of high modulus films of relatively thinner gage include higher strength, good machine processing characteristics with an acceptable amount of stretch, reduced caliper and less cost, lesser tendency to shatter, and significantly lower film rigidity since the rigidity is proportional to the cube of the film thickness.

As noted above, the adhesive layer 40 may be a known adhesive material such as pressure-sensitive adhesives including acrylic resin and natural or synthetic based rubber adhesives. Preferred adhesives include hot melt pressure-sensitive adhesives of the A-B-A block copolymer type comprising an elastomeric B-block derived from isoprene and thermoplastic A-blocks derived from styrene as disclosed in U.S. Pat. No. 3,932,328. Illustrative rubber based adhesives include styrene-isoprene-styrene and styrene-butadiene-styrene which may optionally contain diblock components such as styrene isoprene and styrene butadiene. It is also possible to use adhesives of different compositions at opposed terminal ends of the tabs to provide factory and user joints of different adhesives. The adhesives may be applied using hot-melt, solvent or emulsion techniques. The adhesive layer 40 may be directly coated onto the film 38 or transfer coated using known techniques. The adhesive layer may range from about 0.5 to 2.5 mils in thickness.

The release layer 36 may be of known compositions such as silicones, vinyl carbamates and acrylics. The release layer may be applied using conventional application techniques such as roll or gravure coating. Typical coating weights range from 0.2 to 2 grams/meter$^2$. The release layer does not interfere with the softness improvements obtained by the surface morphologies of the invention.

Referring to FIG. 3, a modified fastener tab 50 is shown. The tab 50 includes release layer 36 and adhesive layer 40 which are identical with those described above in connection with the fastener tab 30. However, the tab 50 includes a multilayer substrate or backing film 52 having a top layer 54 and bottom layer 56 integrally and uniformly joined along an interior interface 58. The top layer 54 provides an outer or exposed side 60 and the bottom layer 56 provides an inner or adhesive side 62. The top and bottom layers 54 and 56 may be formed of different polymeric materials and/or additives in order to provide different film properties or characteristics at the exposed and adhesive sides of the film 52. For example, the top layer 54 may be formed of an appearance selected polymer and the bottom layer 56 may be a strength selected polymer. The film 52 may be formed by lamination or coextrusion of the two layers 54 and 56. Also, the film 52 may be formed of three layers in an A-B-A arrangement, or more than three layers may be used.

Referring to FIG. 4, a process is shown for the manufacture of a film 70 which may be converted to provide substrate or backing film 38 for use in the tab 30. The film 70 is prepared by extrusion of a suitable resin charge, such as polypropylene homopolymer from an extruder 72 into the nip formed by a rubber back-up roll 74 and an engraved embossing or chill roll 76. The extruded resin may be at a temperature of about 300° F. as it exits the extruder 70 and it is chilled upon contact with the roll 76 which is at a temperature of 60° to 100° F. As the resin passes through the nip and around the roll 76, the film 70 is formed and embossed. Thus, a first side of the film 70 is embossed to provide the desired surface morphology for use as the fastener tab outer side 42 and the second side of the film 70 has a smoother surface for use as the fastener tab adhesive side 44.

The film 70 passes from the roll 76 into a nip formed by a rubber back-up roll 78 and a chill roll 80 to further reduce the temperature of the film. The film is then trained through a pair of corona treatment units 82 to improve the anchorage of the release coat, adhesive layer and any printing which may be applied to the surfaces of the film. The corona treated film 70 is then wound in a roll 84 for storage and further processing.

The continued processing of the film 70 is illustrated in FIG. 5 where the roll 84 is unwound and the film 70 is passed to a release coating station "R" for application of release coat 36 to the embossed side of the film. Thereafter, the adhesive layer 40 is applied to the opposite side of the film 70 at an adhesive coating station "A". The film is then slit at a slitting station "S" in a lengthwise or machine direction to form a plurality of fastener tapes 86. Each of the tapes 86 has a width corresponding with the desired fastener tab length. The tapes are self-wound into fastener tape rolls 88 for further processing or transport. Typically, the fastener tape rolls 88 are converted to fastener tabs 30 by cutting across the width of the tapes 86 during the final steps of diaper manufacture and applied to the diapers using automatic machine processing.

It will be understood that the operations shown in FIGS. 4 and 5 will often be done at different locations by different manufacturers, or they may be combined. For example, the steps shown in FIG. 4 may be done by a film supplier and the steps shown in FIG. 5 may be done by a tape manufacturer.

Referring to FIG. 6, the fastener tab 30 is shown applied to the diaper 10. The fastener tab 30 is cut to a length of about 2.5 to 3" depending upon the diaper size. A first terminal segment 30*a* of the tab 30 is adhered at factory joint 32 to the associated lateral edge of the rear waistband section 20 of the diaper 10. An opposite terminal segment 30*b* of the tab 30 is folded over on itself to form a finger lift 90 for use in deploying the tab from its stored position. For purposes of storing the tab 30, a release tape 92 is adhered to the top sheet 16 of the diaper opposite the factory joint 32. The release tape 92 has a release coating on its outer surface. The over-hanging or extending portion of the tab 30 is folded around the lateral edge of the diaper 10 and removably secured to the release coating on the tape 92 for temporary storage of the tab prior to its deployment to a diaper fastening position at user joint 30 on the landing zone 26 of the reinforcing tape 24.

Referring to FIG. 7, the fastener tab 30 is shown applied to the diaper 10 using a "Y-bond" mounting arrangement. In this instance, the release tape 92' has a longer length. More particularly, the release tape 92' extends beyond the lateral extremity of the diaper 10 and into engagement with an adjacent portion of the adhesive layer 40.

In the following Table I, Examples 1–10 of specific fastener tab substrate films further illustrate the invention and comparative Example 1C and 2C illustrate known prior art substrate films. The films were prepared using the processes of FIGS. 4 and 5 unless otherwise noted. The physical properties reported in Table I were measured at least seven days after film manufacture. The strength of these films as characterized by the reported modulus and yield point values indicates machine processability at customary conditions.

The films of Examples 1–9 and Comparative Examples 1C and 2C were formed by extruding charges of polypropylene homopolymer (PP), polyethylene homopolymer (PE), and blends or copolymers thereof as indicated below. The extruded films were immediately embossed using either a 45 RMS or 250 RMS random pattern embossing roll formed by sand blasting a steel roll and applying a chrome finish coat finish to the roll embossing surface.

The film of Example 10 was formed using a biaxially oriented polypropylene film sold under the designation TORAYFAN by Toray Plastics America, Inc. of North Kingston, R.I. This film is believed to comprise a laminate of three polypropylene layers, and it is available in thicknesses ranging from about 1 to about 3 mils. A suitable surface roughness results from the manufacturing process without a separate embossing step.

Each of the films of the examples and comparative examples was combined with an adhesive layer of hot melt pressure-sensitive adhesive of the A-B-A block copolymer type as disclosed in U.S. Pat. No. 3,932,328. One specific adhesive formulation is set forth below.

| Component | Weight Percent |
| --- | --- |
| Kraton 1107 | 31.7 |
| Escorez 1310 LC2 | 46.3 |
| Wingtack 10 | 19.8 |
| Ethanox 330 | 1.0 |
| Plastonox LDTP | 0.9 |

KRATON 1107 is a polystyrene-isoprene-polystyrene linear block copolymer sold by Shell Chemical Co. ESCOREZ 1310 LC is a solid $C_5$ tackifying resin sold by Exxon Chemical Corp. WINGTACK 10 is a solid $C_5$ tackifying resin sold by Goodyear Chemical Co. ETHANOX 330 is a phenolic antioxidant sold by Ethyl Corporation. PLASTONOX LDTP is a thioester antioxidant sold by American Cyanamid Company.

The films of Examples 1–10 have satisfactory tactile and pliant softness characteristics based on finger touching the film surface and hand manipulation of the film. The films of Comparative Examples 1C and 2C do not have satisfactory pliant softness as measured by hand manipulation of the film. The films of Comparative Examples 1C and 2C were also determined to be of a lesser tactile softness than the films of Examples 1–10 as determined by finger touching of the film surfaces and indicated by the Ra values.

TABLE I

| Example Number | Film Polymer | Gage[1] (mils) | Yield[2] (#/in.) | Modulus[3] (psi) | Ra (Å) |
| --- | --- | --- | --- | --- | --- |
| 1 | PP | 3.30 | 8.88 | 88930 ± 1680 | 9000–13000[8] |
| 2 | PP | 4.74 | 14.01 | 88990 ± 7990 | 9000–13000[8] |
| 3 | PP | 6.47 | 18.92 | 74410 ± 5930 | 9000–13000[8] |
| 4 | PP/PE[4] | 3.36 | 7.10 | 65840 ± 3700 | 9000–13000[8] |
| 5 | PP/PE[4] | 5.01 | 11.10 | 61890 ± 2460 | 9000–13000[8] |
| 6 | PP/PE[4] | 6.58 | 14.78 | 56440 ± 3340 | 9000–13000[8] |
| 7 | PE | 3.38 | 4.27 | 19040 ± 330 | 9000–13000[8] |
| 8 | PE | 5.00 | 6.23 | 19690 ± 360 | 9000–13000[8] |
| 9 | PE | 6.62 | 8.45 | 19620 ± 60 | 9000–13000[8] |
| 10 | PP[5] | 1.00 | — | 250000[7] | 8720–10720 |
| 1C | PP | 4.27 | 12.77 | 99560 ± 1865 | 68830–75830[9] |
| 2C | PP/PE[6] | 4.60 | 11.36 | 79440 ± 2490 | 68830–75830[9] |

[1]Yield average gage - ASTM E252-84.
[2]Cross-direction yield point - ASTM D4321-83.
[3]Cross-direction modulus - ASTM D882-88.
[4]50/50 blend.
[5]Three layer laminate.
[6]Random copolymer of PP and 2.5% PE.
[7]Film manufacturer data.
[8]Estimate based on use of 45 RMS roll.
[9]Estimate based on use of 250 RMS roll.

It is presently believed that the films of the invention may have a cross-direction (CD) modulus as low as 19,500 psi and a cross-direction yield point of about 4 lbs./inch or higher. More preferably, the cross-direction modulus is about 24,000 psi and the cross-direction yield point is about 6 lbs./inch or higher. The most preferred films have a cross-direction modulus of about 80,000 psi or higher and a cross-direction yield point of about 9.0 lbs./inch or higher. Referring to FIG. 8, the surface of an outer side of a substrate film of a fastener tab in accordance with the invention is shown at 100× magnification. As indicated above, this film was formed of an extruded polypropylene homopolymer which was embossed with a 45 RMS chrome coated steel embossing roll. The Ra value ranges from 7,070 to 14,610 angstroms, and the surface is characterized by a large number of closely spaced discrete projections or asperities of generally uniform height.

Figure 9:
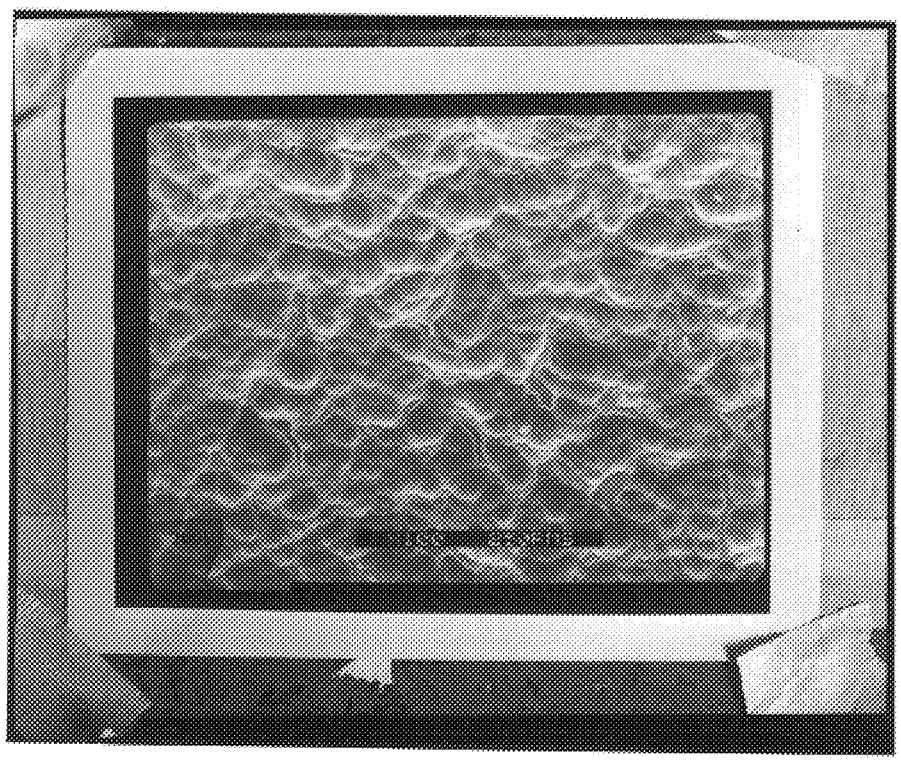
FIG. 9 is a photomicrograph at 100× magnification of an outer surface of a prior art polymeric substrate film for a fastener tab.

Referring to FIG. 9, the surface of an outer side of a prior art fastener tab in accordance with Example 2C is shown at 100× magnification. This film was extruded and embossed with a 250 RMS roll so as to result in a Ra value of about 72,330±3,500 angstroms. This film surface is characterized by intersecting or overlapping projections yielding an orange peel appearance. The projections are substantially larger than those obtained in accordance with the invention.

While the invention has been shown and described with respect to particular embodiments thereof, this is for the purpose of illustration rather than limitation, and other variations and modifications of the specific embodiments herein shown and described will be apparent to those skilled in the art all within the intended spirit and scope of the invention. For example, although illustrated in respect to reinforced diapers, the invention also contemplates non-reinforced diaper applications wherein the tab is fastened closed by direct adhesive closure to the diaper shell. Accordingly, the patent is not limited in scope and effect to the specific embodiments herein shown and described nor in any other way that is inconsistent with the extent to which the progress in the art has been advanced by the invention.

What is claimed is:

1. A method of making a fastening tape adapted to be converted into a fastener tab for a disposable diaper or other tab fastened article, said tape having an indefinite length extending in a machine direction, a width extending in a machine cross direction and a thickness, comprising the steps of providing a polymeric resin film substrate or tape backing having an outer side and an inner adhesive side, roughening the outer side to form an outer film surface morphology on said outer side having a roughness average value of from about 7,000 to about 14,700 angstroms, joining a layer of adhesive to said inner adhesive side of said film, converting said tape by cutting it to form a tab fastener having a length extending in the machine cross direction with opposed terminal segments spaced apart in the machine cross direction.

2. The method of claim 1, wherein the step of roughening said outer side includes embossing said film to form said outer film surface morphology.

3. The method of claim 2, wherein the step of providing said film includes extruding a film forming resin to form said film.

4. The method of claim 1, wherein the extruding step immediately precedes the embossing step.

5. The method of claim 2, further including the step of joining a second layer of adhesive to said film at said inner adhesive side of said film along a second machine cross direction segment of said film spaced from said first mentioned machine cross direction segment, and the step of converting said tape provides said first mentioned layer of adhesive adjacent said first mentioned terminal segment and said second layer of adhesive adjacent said second terminal segment.

* * * * *